United States Patent
Etchegaray et al.

(10) Patent No.: US 6,413,542 B1
(45) Date of Patent: *Jul. 2, 2002

(54) DIRECT POUR-ON ANTIPARASITIC SKIN SOLUTION AND METHODS FOR TREATING, PREVENTING AND CONTROLLING MYASIS

(75) Inventors: Jean-Pierre Etchegaray, Toulouse; Philippe Jeannin, Tournefeuille, both of (FR)

(73) Assignee: Merial, Lyon (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/450,186

(22) Filed: Nov. 29, 1999

Related U.S. Application Data

(63) Continuation-in-part of application No. 08/933,016, filed on Sep. 18, 1997, now Pat. No. 6,010,710, which is a continuation-in-part of application No. 08/692,178, filed on Aug. 5, 1996, now abandoned, application No. 09/450,186, which is a continuation-in-part of application No. 09/051,693, filed as application No. PCT/FR97/01504 on Aug. 19, 1997, now Pat. No. 6,001,384.

(30) Foreign Application Priority Data

Mar. 29, 1996 (FR) ............................................. 96 04209
Aug. 20, 1996 (FR) ............................................. 96 10312
Mar. 26, 1997 (FR) ............................................. 97 03708

(51) Int. Cl.$^7$ ............................................. A01N 25/02
(52) U.S. Cl. ................... 424/438; 424/405; 424/406; 424/407; 514/406; 514/407
(58) Field of Search ................................. 424/405, 406, 424/438; 514/407, 406, 875, 919, 937, 946, 947, 970, 971

(56) References Cited

U.S. PATENT DOCUMENTS

4,963,575 A    10/1990   Buntain et al.

(List continued on next page.)

FOREIGN PATENT DOCUMENTS

EP    0 295 117 A1   12/1988

(List continued on next page.)

OTHER PUBLICATIONS

Bloomquist, J.R., Ion Channels as Targets for Insecticides, *Annu. Rev. Entomol.*; vol. 41, 163–90 (1996).

(List continued on next page.)

*Primary Examiner*—Neil S. Levy
(74) *Attorney, Agent, or Firm*—Frommer Lawrence & Haug, LLP; William S. Frommer; Thomas J. Kowalski (57) ABSTRACT

The direct pour-on skin solution intended to eliminate parasites, in particular *Boophilus microplus*, from cattle and sheep comprises from 0.05 to 25%, preferably from 0.05 to 10%, and in particular from 0.1 to 2% weight/volume, relative to the total solution, of a compound of formula (I):

(I)

in a formulation at low volume, designed to release the compound (I) onto the skin and the hairs for a contact action against parasites.

32 Claims, 2 Drawing Sheets

U.S. PATENT DOCUMENTS

| | | |
|---|---|---|
| 5,122,530 A | 6/1992 | Tomioka et al. |
| 5,232,940 A | 8/1993 | Hatton et al. |
| 5,516,787 A | 5/1996 | Takada |
| 5,567,429 A | 10/1996 | Senbo |
| 5,629,334 A | 5/1997 | Takada |
| 5,801,189 A | 9/1998 | Twinn |
| 5,885,607 A | 3/1999 | Jeannin |
| 6,001,384 A | 12/1999 | Jeannin |
| 6,010,710 A | 1/2000 | Etchegaray |

FOREIGN PATENT DOCUMENTS

| | | |
|---|---|---|
| WO | WO 98/24769 | 6/1998 |
| WO | WO 98/39972 | 9/1998 |

OTHER PUBLICATIONS

Hainzl, D. et al, Mechanisms for Selective Toxicity of Fipronil Insecticide and Its Sulfone Metabolite and Desulfinyl Photoproduct, *Chem. Res. Toxicol*; vol. 11(12), 1529–35 (1998).

Hainzl, D. et al, Fipronil Insecticide: Novel Photochemical Desulfinylation with Retention of Neurotoxicity, *Proc. Natl. Acad. Sci. USA*; Nov. 12;93(23), 12764–7 (1996).

Cochet, P. et al, Skin Distribution of Fipronil by Microautoradiography following Topical Administration to the Beagle Dog, *Eur. J. Drug Metab. Pharmacokinet*. Jul.–Sep.; 22(3): 211–6 (1997).

DIRECT POUR-ON ANTIPARASITIC SKIN SOLUTION AND METHODS FOR TREATING, PREVENTING AND CONTROLLING MYASIS

This application is a continuation-in-part of U.S. application Ser. No. 08/933,016, filed Sep. 18, 1997, now allowed, U.S. Pat. No. 6,010,710 which is in turn a continuation-in-part of application U.S. Ser. No. 08/692,178, filed Aug. 5, 1996, now abandoned, which claims priority to, French patent application No. 96 04 209 filed Mar. 29, 1996, and French patent application No. 97 03 708 filed Mar. 26, 1997; and this application is also a continuation-in-part of U.S. application Ser. No. 09/051,693, filed Jul. 27, 1998, now allowed, U.S. Pat. No. 6,001,384 which in turn is the National Phase of International Application PCT/FR97/01504 having an international filing date of Aug. 19, 1997, and designating the U.S. and claiming priority from French patent application No. 96 10 312, filed Aug. 20, 1996.

Reference is also made to: U.S. application Ser. No. 09/271,470 filed Mar. 17, 1999, now pending, which is a continuation-in-part of International Application PCT/FR97/01548, having an international filing date of Sep. 15, 1997 and designating the U.S., and claiming priority to French application No. 96 11 446 filed Sep. 19, 1996; U.S. application Ser. No. 09/376,736, filed Aug. 17, 1999, now pending, which is a continuation-in-part of U.S. application Ser. No. 09/271,470 filed on Mar. 17, 1999, now pending, which is a continuation-in-part of International Application PCT/FR97/01548, having an international filing date of Sep. 15, 1997 and designating the U.S., and claiming priority to French application No. 96 11 446 filed Sep. 19, 1996; U.S. application Ser. No. 09/381,794, filed Sep. 24, 1999, now pending, which in turn is the National Phase of International Application No. PCT/FR98/00601 having an international filing date of Mar. 25, 1998 and designating the U.S., and claiming priority to French application No. 97 03 709, filed Mar. 26, 1997; U.S. application Ser. No. 08/891,047, filed Jul. 10, 1997, now pending, which claims priority from French application No. 96 08 703 filed Jul. 11, 1996 and French application No. 97 03 025 filed Mar. 13, 1997; U.S. application Ser. No. 08/863,692 filed Mar. 27, 1997, now allowed, which is a continuation-in-part of U.S. application Ser. No. 08/692,113 filed Aug. 5, 1996, now abandoned, which claims priority to French patent application 96 04 208, filed Mar. 29, 1996 and French application No. 97 03 711 filed Mar. 26, 1997; U.S. application Ser. No. 08/719,942 filed Sep. 25, 1996, which claim priority to French application No. 95 11 685 filed Sep. 29, 1995 and French application No. 96 11 278 filed Sep. 11, 1996; and U.S. application Ser. No. 09/174,598 filed Oct. 19, 1998, now pending, which is a divisional application of U.S. application Ser. No. 08/863,182 filed Mar. 27, 1997, now U.S. Pat. No. 5,885,607, which is a continuation-in-part of U.S. application Ser. No. 08/692.430 filed Aug. 5, 1996, now abandoned, and which claims priority to French application No. 96 04 206 filed Mar. 29, 1996 and French application No. 97 03 707 filed Mar. 26, 1997.

Each of the herein cited patent applications, and all documents cited in the text or during the prosecution of the herein cited patent applications ("application cited documents")—either cited by the Examiner (e.g., Patent Office, such as the U.S. or French Patent Office or WIPO or Searching Authority) or by the applicant(s)—as well as all documents cited or referenced in application cited documents, are hereby incorporated herein by reference.

Further, all documents cited herein ("herein cited documents") and all documents cited or referenced in herein cited documents are hereby incorporated herein by reference.

Further, the following documents are hereby incorporated herein by reference:

U.S. Pat. No. 5,885,607, issued to Jeannin on Mar. 23, 1999;
U.S. Pat. No. 5,801,189, issued to Twinn on Sep. 1, 1998;
U.S. Pat. No. 5,232,940, issued to Hatton on Aug. 3, 1993;
U.S. Pat. No. 5,122,530, issued to Tomioka on Jun. 16, 1992;
U.S. Pat. No. 5,567,429, issued to Senbo on Oct. 22, 1996;
U.S. Pat. No. 4,963,575, issued to Buntain on Oct. 16, 1990;
U.S. Pat. No. 5,516,787, issued to Takada on May 14, 1996;
U.S. Pat. No. 5,629,334, issued to Takada on May 13, 1997;
EP 0 295 117 with an international filing date of Jun. 10, 1988;
PCT/EP98/01224 with an international filing date of Mar. 1, 1998;
PCT/EP97/06503 with an international filing date of Nov. 21, 1997;
Bloomquist, J.R., *Ion Channels as Targets for Insecticides*, Annu. Rev. Entomol.; Vol. 41,163–90 (1996);
Hainzl, D. et al, *Mechanisms for Selective Toxicity of Fipronil Insecticide and Its Sulfone Metabolite and Desulfinyl Photoproduct*, Chem. Res. Toxicol; Vol. 11(12), 1529–35 (1998);
Hainzl, D. et al, *Fipronil Insecticide. Novel Photochemical Desulfinylation with Retention of Neurotoxicity*, Proc. Natl. Acad. Sci. USA; Nov. 12, 1993 (23), 12764–7 (1996); and
Cochet, P. et al, *Skin Distribution of Fipronil by Microautoradiogaphy following Topical Administration to the Beagle Dog*, Eur. J. Drug Metab. Pharmacokinet. July-September; 22(3): 211–6 (1997).

This invention envisions compounds, compositions, formulations and methods of use involving a phenylpyrazole as depicted herein or in herein cited documents; and phenylpyrazoles depicted herein or in herein cited documents can be used in the compositions, formulations and methods of herein cited patent applications. Further, the invention envisions compounds that degrade, e.g., biodegrade or photodegrade or chemically degrade, to phenylpyrazoles as depicted herein or in herein cited documents or to same or similar derivatives of phenylpyrazoles herein depicted from degradation (e.g., biodegradation, photodegradation, chemical degradation); for instance, if a herein depicted phenylpyrazole degrades to compound "X", the invention envisions compounds "X" and other phenylpyrazoles that degrade to compound "X". The invention also envisions compositions, formulations, and methods of use involving compounds that degrade to phenylpyrazoles as depicted herein or in herein cited documents or to same or similar derivatives of phenylpyrazoles herein depicted from degradation; for example, pour-on formulations, spot-on formulations, formulations and/or methods for distribution in sebacious glands, formulations and/or methods of preventing, treating, controlling, and/or combating myasis, and the like, as well as in compositions, formulations, and uses of herein cited patent applications. (A compound that degrades to a phenylpyrazole herein depicted or that degrades to a same or similar derivative of a phenylpyrazole herein depicted from degradation, e.g., a phenylpyrazole that degrades to compound "X" that is a degradation derivative of a herein depicted phenylpyrazole is herein termed a "pro-pp-compound".) More in particular, herein depicted phenylpyrazoles as well as those of documents cited herein, e.g., PCT/EP97/06503 or WO 98/24769, degrade to the active compound fipronil sulfide (sulfide on the 4 position) and thus, the invention comprehends the use of phenylpyrazoles depicted herein and in documents cited herein that degrade to fipronil sulfide, in for example, pour-on formulations, spot-on formulations, formulations and/or methods for distribution in sebacious glands, formulations and/or methods of preventing, treating, controlling, and/or combating myasis, and the like, as well as in compositions, formulations, and uses of herein cited patent applications. Ethaprol (or a 4-ethylsulfoxide derivative of herein depicted phenylpyrazole) as well as compounds of the herein formula wherein there is a sulfide at the 4 position and/or $R_1$=CN, SO and/or $R_3$=$CF_3$ or alkyl (e.g., 4-haloalkyl sulfoxide sulfones, 3-cyanos, 3-cyano-pro-pp-compounds) are useful, e.g., in pour-on formulations and methods. Formulations, compositions and methods of use can include a additional active ingredient, such as a macrolide antibiotic and/or an insect growth regulator (IGR); or the like, which can be admixed with or administered separately from, e.g., sequentially, with the phenylpyrazole and/or pro-pp-compound (or the macrolide antibiotic and/or IGR can itself, without the phenylpyrazole and/or pro-pp-compound, be the active ingredient in the formulation, such as pour-on or spot-on formulation or a formulation for distribution in the sebacious glands, as disclosed herein or in herein cited patent applications). These and other embodiments are provided in this text.

The present invention relates to a direct pour-on skin solution which contains an antiparasitic product and is intended to be applied topically to cattle and sheep.

The invention also relates to the use of antiparasitic compounds for the preparation of this skin solution, as well as to a treatment process relating thereto.

Cattle and sheep are affected by a large number of parasites.

The main ones are ticks of the genus Boophilus, among which mention may be made of the species microplus (cattle tick), decoloratus and anulatus.

The other main parasites of cattle and sheep are indicated in order of decreasing importance:

myiases such as *Dermatobia hominis* (known as Berne in Brazil) and *Cochlyomia hominivorax* (greenbottle); sheep myiases such as *Lucilia sericata, Lucilia cuprina* (known as blowfly strike in Australia, New Zealand and South Africa). These are flies whose larva constitutes the animal parasite.

flies proper, namely those whose adult constitutes the parasite, such as *Haematobia irritans* (horn fly).

lice such as *Linognathus vitulorum*, etc. galls such as *Sarcoptes scabiei* and *Psoroptes ovis*.

Ticks, in particular *Boophilus microplus*, are very closely attached to the pasture in which they live and are particularly difficult to control.

There is at the present time no truly effective method for controlling ticks, and less still an effective way of controlling the set of parasites indicated above.

N-phenyl derivatives have been disclosed as a class of insecticides whose compositions include: 1-arylpyrazoles (e.g. 1-(2,6-dichloro-4-trifluoromethylphenyl)-5-methylamino-4-trifluoromethylthio-pyrazole or 1-(2,6-dichloro-4-trifluoromethylphenyl)-5-methylamino-4-dichlorofluoromethylthio-pyrazole); and 1-(substituted phenyl or pyridyl)-substituted pyrazole (e.g. 1-[2-(-3-chloro-5-trifluoromethyl)pyridyl]-3-cyano-4-chlorodifluoromethylsulfenyl-5-aminopyrazole, 1-[2-(3-chloro-5-trifluoromethyl)pyridyl]-3-ethoxycarbonyl-5-aminopyrazole, 1-[2-(3-chloro-5-trifluoromethyl)pyridyl]-3-cyano-4-chlorodifluormethylsulfinyl-5-aminopyrazole and 1-[2-(3-chloro-5-trifluoromethyl)pyridyl]-3-cyano-4-chlorodifluoromethylsulfonyl-5-aminopyrazole). These compounds are given as having activity against a very large number of parasites, including *Boophilus microplus*, in fields as varied as agriculture, public health and veterinary medicine. These insecticidal compounds may be administered via different routes; oral, parenteral, percutaneous, and topical routes. Topical administration comprises, in particular, oral formulations, baits, dietary supplements, skin solutions (pour-on), solutions for spraying (sprays), baths, showers, jets, powders, greases, shampoos, creams, etc. The pour-on type skin solutions are designed for percutaneous administration. As described in foreign patents EP-A-295,117 and EP-A-500,209 (specifically in Examples 9 and 291, respectively), a typical example of a pour-on skin solution could contain 15% insecticide and 85% dimethyl sulphoxide, formulated for percutaneous administration of the insecticide.

Other compounds including 5-methylamino-1-arylpyrazoles (e.g. 1-(2,6-dichloro-4-trifluoromethylphenyl)-5-methylamino-4-dichlorofluoromethylthio-pyrazole or 1-(2,6-dichlo-4-trifluoromethylphenyl)-5-methylamino-4-trifluoromethylthio-pyrazole) have been described as having insecticidal activity in the field of agriculture, public health and veterinary medicine. *Boophilus microplus* is one of the very many targets mentioned. There are very many forms of administration here also, and these include, for example, solutions, emulsions, suspensions, powders, pastes, granules and aerosols.

The problem which is posed is to find an effective means which is entirely suitable for controlling the parasites of cattle and sheep, in particular ticks, most particularly *Boophilus microplus* in cattle and in particular lice and blowfly in sheep, under the conditions in which these animals are reared.

The Applicant has found that it is possible to effectively control *Boophilus microplus* for cattle using a specific topical formulation. The Applicant has also found that this formulation is effective against sheep lice and sheep flies known as "blowfly".

The aim of the present invention is thus to provide a novel composition which is entirely effective against *Boophilus microplus* and also against all of the other parasites described above such as, in particular, sheep lice and "blowfly", this composition being entirely suitable for controlling these parasites under the conditions in which these animals are reared.

Another aim of the invention is to provide such a formulation which has a long period of efficacy, preferably longer than or equal to two months.

Another aim of the invention is to provide such a formulation which is quick and easy to use and entirely compatible with use on herds or flocks containing a large number of animals.

Another aim of the invention is to provide such a formulation which is particularly suitable for extensive pasture rearing and for use intended to protect animals during the period of rounding up and finishing (Feed Lot in USA), namely the final period of rearing in which a large number of animals are herded into a small enclosure over an average period of two months preceding slaughter.

The subject of the present invention is thus a direct pour-on skin solution, intended to eliminate parasites from cattle and sheep, most particularly ticks, especially *Boophilus microplus* in cattle and lice and blowfly in sheep, comprising from 0.05 to 25% weight/volume, relative to the total solution, of a compound of formula (I)

in which:
- $R_1$ is CN or methyl or a halogen atom;
- $R_2$ is $S(O))_n R_3$ or 4,5-dicyanoimidazol-2-yl or haloalkyl;
- $R_3$ is alkyl or haloalkyl;
- $R_4$ represents a hydrogen or halogen atom; or a radical $NR_5R_6$, $S(O)_m R_7$, $C(O)R_7$, $C(O)O—R_7$, alkyl, haloalkyl or $OR_8$ or a radical $—N=C(R_9)(R_{10})$;
- $R_5$ and $R_6$ independently represent a hydrogen atom or an alkyl, haloalkyl, C(O)alkyl, alkoxycarbonyl or $S(O)_r CF_3$ radical; or $R_5$ and $R_6$ may together form a divalent alkylene radical which may be interrupted by one or two divalent hetero atoms, such as oxygen or sulphur;
- $R_7$ represents an alkyl or haloalkyl radical;
- $R_8$ represents an alkyl or haloalkyl radical or a hydrogen atom;
- $R_9$ represents an alkyl radical or a hydrogen atom;
- $R_{10}$ represents a phenyl or heteroaryl group optionally substituted with one or more halogen atoms or groups such as OH, —O-alkyl, —S-alkyl, cyano or alkyl;
- $R_{11}$ and $R_{12}$ represent, independently of each other, a hydrogen or halogen atom, or optionally CN or $NO_2$;
- $R_{13}$ represents a halogen atom or a haloalkyl, haloalkoxy, $S(O)_q CF_3$ or $SF_5$ group;
- m, n, q, and r represent, independently of each other, an integer equal to 0, 1 or 2;
- X represents a trivalent nitrogen atom or a radical C—$R_{12}$, the other three valency positions of the carbon atom forming part of the aromatic ring;
- with the proviso that, when $R_1$ is methyl, either $R_3$ is haloalkyl, $R_4$ is $NH_2$, $R_{11}$ is Cl, $R_{13}$ is $CF_3$ and X is N; or $R_2$ is 4,5-dicyanoimidazol-2-yl, $R_4$ is Cl, $R_{11}$ is Cl, $R_{13}$ is $CF_3$ and X is =C—Cl;

in a formulation at low volume, designed to release the compound (I) onto the skin and the hairs for a contact action against parasites.

Preferably, in formula (I),
- $R_1$ is CN or methyl;
- $R_2$ is $S(O)_n R_3$;
- $R_3$ is alkyl or haloalkyl;
- $R_4$ represents a hydrogen or halogen atom; or a radical $NR_5R_6$, $S(O)_m R_7$, $C(O)R_7$, alkyl, haloalkyl or $OR_8$ or a radical $—N=C(R_9)(R_{10})$;
- $R_5$ and $R_6$ independently represent a hydrogen atom or an alkyl, haloalkyl, C(O)alkyl or $S(O)_r CF_3$, radical; or $R_5$, and $R_6$ may together form a divalent alkylene radical which may be interrupted by one or two divalent hetero atoms, such as oxygen or sulphur;
- $R_7$ represents an alkyl or haloalkyl radical;
- $R_8$ represents an alkyl or haloalkyl radical or a hydrogen atom;
- $R_9$ represents an alkyl radical or a hydrogen atom;
- $R_{10}$ represents a phenyl or heteroaryl group optionally substituted with one or more halogen atoms or groups such as OH, —O-alkyl, —S-alkyl, cyano or alkyl;
- $R_{11}$ and $R_{12}$ represent, independently of each other, a hydrogen or halogen atom;
- $R_{13}$ represents a halogen atom or a haloalkyl, haloalkoxy, $S(O)_q CF_3$ or $SF_5$, group;
- m, n, q, and r represent, independently of each other, an integer equal to 0, 1 or 2;
- X represents a trivalent nitrogen atom or a radical C—$R_{12}$, the other three valency positions of the carbon atom forming part of the aromatic ring;
- with the proviso that, when $R_1$ is methyl, then $R_3$ is haloalkyl, $R_4$ is $NH_2$, $R_{11}$ is Cl, $R_{13}$ is $CF_3$ and X is N.

However, low concentrations of from 0.05 to 10% weight/volume, more particularly from 0.1 to 2%, are preferred. Optimally, the value is between 0.25 and 1.5%, in particular in the region of 1%.

The expression pour-on skin solution is understood to refer to a ready-to-use solution intended to be applied topically and locally on the animal, preferably on the animal's back and at several points or along the line of the back, and applied in low volume, preferably of 5 to 20 ml per 100 kg, preferably about 10 ml per 100 kg, with a total volume of from 10 to 150 ml per animal, preferably limited to 50 ml.

The compound acts by simple contact, the parasite becoming impregnated with the compound on contact with the hairs and the skin.

This thereby affords, in a noteworthy manner, a both perfect compatibility with the restrictions of use in extensive grazing, in terms of ease of use in particular, and a spectrum of activity and of efficacy, as well as a period of efficacy, which are suited to this type of rearing.

By working on the concentration of compound (I), in particular of compound A, solutions having noteworthy activities are obtained with, in particular, two months of efficacy against *Boophilus microplus*, this result never before having been achieved. Moreover, the solution according to the invention allows *Boophilus microplus* to be totally eliminated from an infested animal in less than 2 days.

As has been stated above, the solution according to the present invention is applied topically, in low volume, to the animal's back. The compound of formula (I) then diffuses out in a noteworthy manner, this being reflected by a distribution of the compound over the animal's entire body. It has also been observed that the animals remained protected in the case of passage through water or exposure to rain.

The dose of compound of formula (I) is preferably between 0.1 and 2 mg/kg (animal weight), preferably between 0.25 and 1.5 mg/kg, and in particular about 1 mg/kg.

The compounds of formula (I) in which $R_1$ is CN will be selected most particularly. The compounds in which $R_2$ is $S(O)_n R_3$, preferably with n=1, $R_3$ preferably being $CF_3$ or alkyl, for example methyl or ethyl, or alternatively n=0, $R_3$ preferably being $CF_3$, as well as those in which X=C—$R_{12}$, $R_{12}$ being a halogen atom, will also be selected. The compounds in which $R_{11}$ is a halogen atom and those in which $R_{13}$ is haloalkyl, preferably $CF_3$, are also preferred. In the context of the present invention, compounds combining two or more of these characteristics will advantageously be selected.

A preferred class of compounds of formula (I) consists of compounds such that $R_1$ is CN, $R_3$ is haloalkyl, preferably $CF_3$, or ethyl, $R_4$ is $NH_2$, $R_{11}$ and $R_{12}$ are, independently of each other, a halogen atom, and/or $R_{13}$ is haloalkyl.

In the present invention, the alkyl radicals may contain generally from 1 to 6 carbon atoms. The cycle formed between the divalent alkylene radical representing $R_5$ and $R_6$, as well as with the nitrogen atom to which $R_5$ and $R_6$ are attached, may be generally a cycle of 5, 6 or 7 links.

A most particularly preferred compound of the formula (I) in the invention is 1-[2,6-$Cl_2$ 4-$CF_3$phenyl]3-CN 4-[SO-$CF_3$]5-$NH_2$pyrazole, referred to hereinbelow as compound A. This compound A will be used in particular in a proportion of from 0.1 to 2% by weight, more particularly about 1%, relative to the total solution.

Mention may also be made of the two compounds which differ from the above by the following characteristics:
1−n=0, $R_3$=$CF_3$
2−n=1, $R_3$=ethyl.

The compounds of formula (I) may be prepared according to one or other of the processes described in patent applications WO-A-87/3781, 93/6089, 94/21606 or European patent application EP-A-0,295,117, or any other process which falls within the competence of a specialist skilled in the art of chemical synthesis. For the chemical preparation of the products of the invention, a person skilled in the art is considered as having at his or her disposal, inter alia, all the contents of "Chemical Abstracts" and the documents cited therein.

It is not departing from the scope of the present invention to incorporate other insecticides into the solution according to the present invention.

The solutions according to the invention, which are advantageously oily, generally comprise a diluent or vehicle and also a solvent (organic solvent) for the compound of formula (I)if the latter is not soluble in the diluent.

As organic solvent which can be used in the invention, mention may be made in particular of: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol and diethyl phthalate, or a mixture of at least two of these solvents.

As vehicle or diluent, mention may be made in particular of:

plant oils such as soybean oil, groundnut oil, castor oil, corn oil, cotton oil, olive oil, grape seed oil, sunflower oil, etc.; mineral oils such as petrolatum, paraffin, silicone, etc.; aliphatic or cyclic hydrocarbons or alternatively, for example, medium-chain (C8 to C12 in particular)triglycerides.

An emollient and/or spreading and/or film-forming agent will preferably be added, this agent being selected in particular from:

polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils, in particular polydimethylsiloxane (PDMS)oils, for example those containing silanol functionalities, or a 45V2 oil, anionic surfactants such as alkaline stearates, in particular sodium, potassium or ammonium stearates; calcium stearate, triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil, cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, amine salts of formula $N^+R'R''R'''$ in which the radicals R are optionally hydroxylated hydrocarbon radicals; octadecylamine hydrochloride is among the cationic surfactants which can be used, nonionic surfactants such as sorbitan esters, which are optionally polyoxyethylenated, in particular polysorbate 80, polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, amphoteric surfactants such as the substituted lauryl compounds of betaine;

or a mixture of at least two of these agents.

The solvent will be used in proportion with the concentration of the compound I and its solubility in this solvent.

For example, compound A has a solubility of 4.3% m/V in acetyl tributyl citrate. It will be sought to have the lowest possible volume.

The vehicle makes up the difference to 100%.

The emollient is preferably used in a proportion of from 0.1 to 10%, in particular from 0.25 to 5%, by volume.

The subject of the present invention is also a process for the elimination of parasites, in particular *Boophilus microplus*, from cattle and sheep using a direct pour-on skin solution according to the present invention, so as obtain long-lasting and broad-spectrum efficacy, the solution being applied to the animal's back, preferably along the line of the back at one or more points.

According to a first embodiment, the process consists in applying the solution to the animals in pasture and/or before they arrive in pasture, the application preferably being repeated every month, preferably every two months.

According to a second embodiment, the process consists in applying the solution to the animals before they arrive in the "feed Lot", it being possible for this application to be the final one before the animals are slaughtered.

Obviously, the process may also consist in combining these two embodiments, namely the first followed by the second.

In all cases, the efficacy advantageously makes it possible to stop any application 1 to 3 months before slaughter, in particular between 1.5 and 2.5 months, more particularly about two months before slaughter.

The solutions according to the invention may be applied using any means known per se, preferably using an applicator gun or a metering flask.

The aim of the method is not therapeutic and is, in particular, to cleanse the skin and the hairs of the animals by eliminating the parasites which are present thereon, as well as their residues and dejections. The result of this is that the animals are no longer stressed by the parasites and their bites, this having positive consequences, for example on their growth and on the use of their food ration.

Another subject of the invention is a therapeutic method using the external device according to the invention, intended for the treatment and prevention of parasitoses having pathogenic consequences.

The subject of the present invention is also the use of the compounds I, in particular compound A, for the manufacture of a direct pour-on skin solution comprising the compound (I)in a low volume and designed to release the compound (I)onto the skin and the hairs for a contact action against the parasites of cattle and sheep, in particular cattle ticks, such as *Boophilus microplus*, and sheep blowfly and lice.

The use according to the invention is directed towards producing skin solutions as described above.

The present invention will now be described in greater detail with the aid of non-limiting embodiment examples which demonstrate the activity of the solutions according to the present invention, with reference to the attached drawings in which.

EXAMPLE 1
Preparation of the Solutions According to the Invention

| Ingredient | Function | Amount |
| --- | --- | --- |
| Compound A | active substance | x g |
| polyoxypropylene 15 stearyl ether | emollient | 5 g |
| acetyl tributyl citrate | solvent | 30 g |
| soybean oil | diluent | qs 100 ml | x = 0.25 g for 0.25% solution
x = 0.5 g for 0.5% solution
x = 1 g for 1% solution Compound A is dissolved in the solvent before being mixed with the other ingredients.

EXAMPLE 2

Study of the efficacy of skin solutions according to the invention containing, respectively, 0.25, 0.50 and 1% compound A to combat *Boophilus microplus*.

The study was performed on 16 young male castrated Herefords (weight ranging between 114 and 172 kg).

Three skin solutions according to Example 1 were prepared:

1. 1% compound A
2. 0.5% compound A
3. 0.25% compound A

A placebo was prepared, which differed from the skin solutions according to the invention in that it contained no compound A.

In the studies, 1 ml of skin solution or of placebo were used per 10 kg of animal weight.

The dose volume was applied along the line of the animal's back, from the head to the base of the tail.

Between days-24 and -1, the animals were artificially infested on 11 occasions with 2,500 *Boophilus microplus* larvae. The aim of 24-day infestation is to ensure that all of the stages of *Boophilus microplus* are present on the animal (eggs, larvae, adults).

On day 0, the animals receive one of the skin solutions or the placebo.

Before the skin solutions or the placebo are applied, the number of ticks present on the various animals in the different groups are counted.

The following table indicates the values recorded, the weight of the animals and the dose of skin solution or of placebo which will be applied to each of these animals.

BRIEF DESCRIPTION OF THE FIGURES

Figure 1:
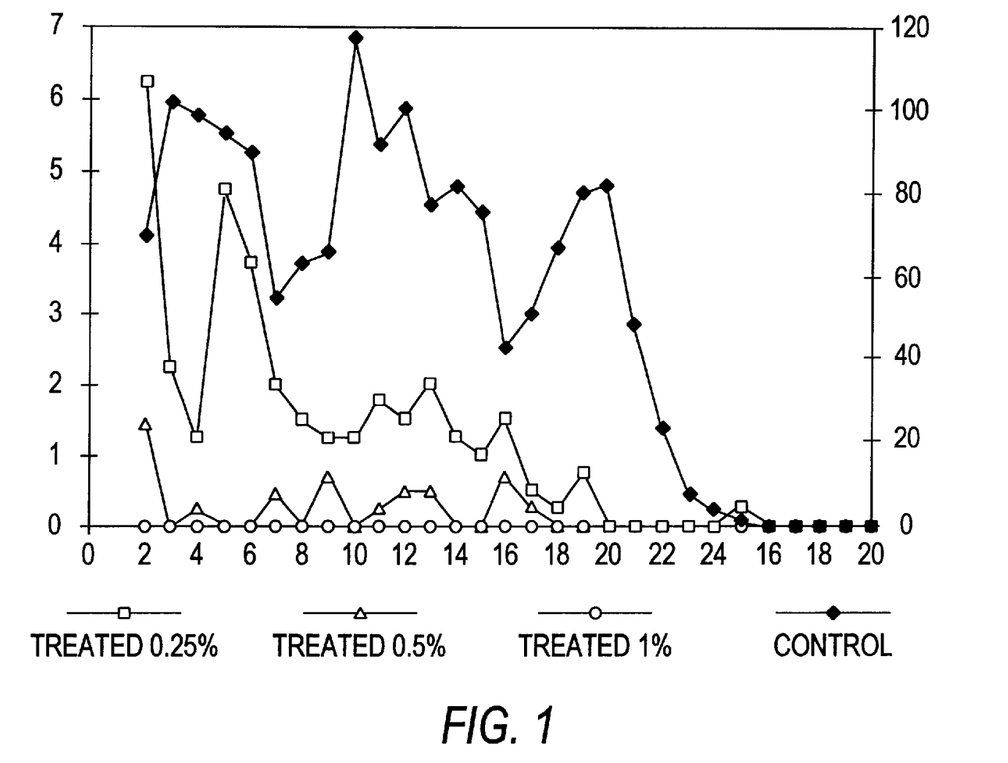
FIG. 1 is a graph showing the efficacy, against *Boophilus microplus*, of skin solutions according to the invention, with a 0.25%, 0.5% and 1% content, relative to a control, this graph including, on the x-axis, the time in days after application of the skin solutions, and, on the y-axis to the left, the number of ticks counted on the animals on which the skin solutions according to the invention are applied, and, on the y-axis to the right, the number of ticks counted in the controls.
Figure 2:
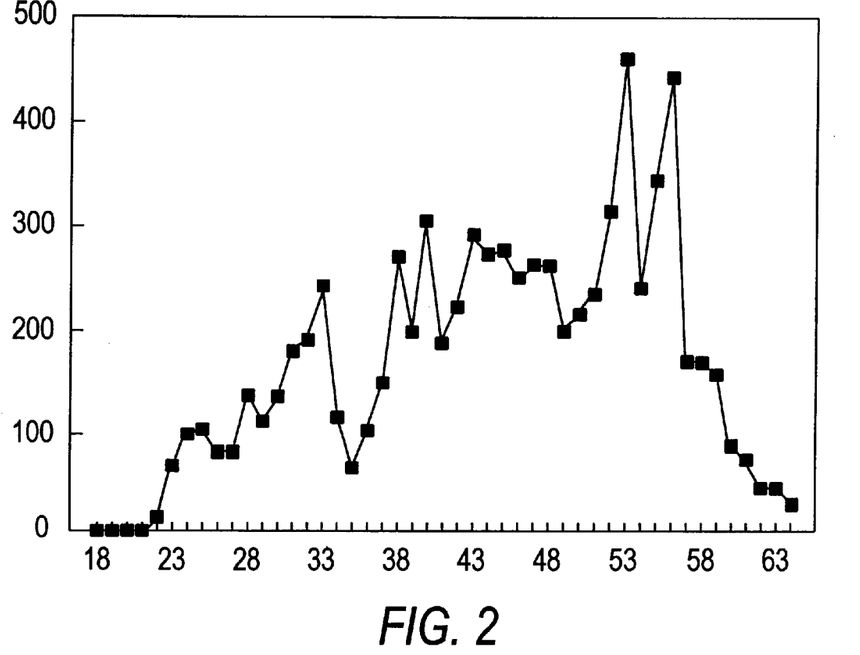
FIG. 2 is a graph showing the population of ticks in animals which have received the placebo according to Example 2, with, on the x-axis, the time-in days, and, on the y-axis, the number of ticks.
Figure 3:
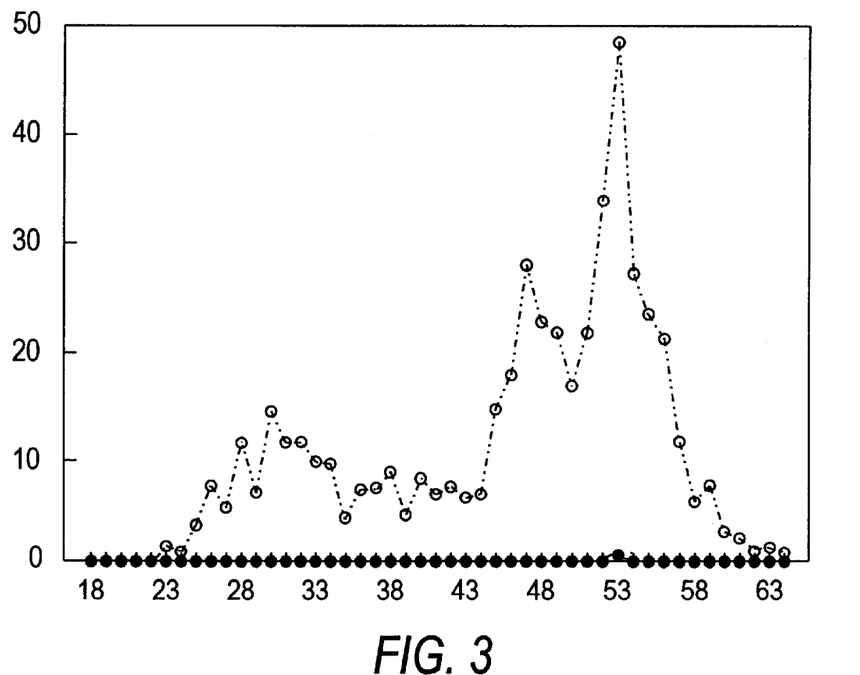
FIG. 3 compares the efficacy of a skin solution according to the invention containing 1% compound A (solid circles) with a skin solution containing 1% flumethrin (rings), with, on the x-axis, the time in days, and, on the y-axis, the number of ticks.

FIG. 1 shows effect on ticks to be dose related.
FIGS. 2 and 3 show control of ticks over 2 months.

| Group | Animal No. | Number of ticks | Weight (in kg) | Dose (ml) |
| --- | --- | --- | --- | --- |
| 1.00% | 94 | 588 | 134 | 13.4 |
| | 43 | 470 | 140 | 14.0 |
| | 47 | 300 | 154 | 15.4 |
| | 39 | 254 | 160 | 16.0 |
| 0.50% | 34 | 706 | 145 | 14.5 |
| | 99 | 452 | 143 | 14.3 |
| | 48 | 375 | 114 | 11.4 |
| | 45 | 201 | 153 | 15.3 |
| 0.25% | 40 | 510 | 148 | 14.8 |
| | 92 | 453 | 144 | 14.4 |
| | 41 | 432 | 155 | 15.5 |
| | 36 | 236 | 171 | 17.1 |
| Placebo | 96 | 627 | 150 | 15.0 |
| | 44 | 482 | 144 | 14.4 |
| | 93 | 315 | 140 | 14.0 |
| | 97 | 292 | 172 | 17.2 |

The blood-engorged female ticks which become detached are included in the count. The results are indicated in FIG. 1.

A dose-dependent effect is obtained with 100% efficacy for the skin solution according to the invention containing 1% compound A. The less-concentrated solutions nevertheless give noteworthy results.

The great rapidity of action of the solutions according to the invention is also noted, the 1% solution allowing *Boopilus microplus* to be totally eliminated in less than 2 days.

EXAMPLE 3

Comparison of efficacy between a skin solution according to the invention containing 1% flumethrin.

Animals of the same breed as those in Example 1 were used.

On day 0, the groups are treated with:
skin solution containing 1% compound A
skin solution containing 1% flumethrin (mineral oil and ethylhexyl alcohol excipient)

placebo (excipient identical to the solution according to the invention)

Table 2 below indicates, for each group, the weight of the animals, the dose of skin solution received and the dose of active substance applied.

| Group | Animal No. | Weight | Dose (ml) | Dose (mg/kg)) |
|---|---|---|---|---|
| 1% | 719 | 141 | 14.1 | 1 |
| Compound A | 709 | 125 | 12.5 | 1 |
| | 713 | 150 | 15.0 | 1 |
| | 710 | 136 | 13.6 | 1 |
| | 703 | 138 | 13.8 | 1 |
| 1% | 706 | 145 | 14.5 | 1 |
| flumethrin | 711 | 136 | 13.6 | 1 |
| | 715 | 132 | 13.2 | 1 |
| | 702 | 142 | 14.2 | 1 |
| | 701 | 127 | 12.7 | 1 |
| Placebo | 717 | 133 | 13.3 | 0 |
| | 707 | 133 | 13.3 | 0 |
| | 704 | 134 | 13.4 | 0 |
| | 718 | 132 | 13.2 | 0 |
| | 708 | 143 | 14.3 | 0 |

From day 2 to day 32, the animals receive 5,000 *Boophilus microplus* larvae three times a week. From day 18 to 64, the blood-engorged female ticks which become detached are collected and counted.

The results are indicated in FIGS. 2 and 3, which demonstrate the total efficacy of the skin solution according to the invention.

EXAMPLE 4

Study of efficacy over time.

Skin solutions according to the invention containing 0.25, 0.5 or 1% compound A where used in this example.

The composition of these solutions is the same as for the above examples.

The cattle were preinfested so as to have all of the stages of *Boophilus microplus* present (infestation with 5,000 larvae, 22 days, 15 days and 8 days before application of the skin solution).

After application of the skin solutions, the cattle are again infested with the larvae for 13 weeks, to determine the efficacy of the three concentrations.

The results are reported in Table 3 below:

| Weeks of infestation after treatment | Efficacy index for each concentration | | |
|---|---|---|---|
| | 0.25% | 0.5% | 1.0% |
| 1 | 97.6 | 100 | 100 |
| 2 | 98.8 | 100 | 100 |
| 3 | 99.7 | 100 | 100 |
| 4 | 99.3 | 100 | 100 |
| 5 | 96.7 | 92.9 | 100 |
| 6 | 98.6 | 93.2 | 100 |
| 7 | 92.4 | 88.6 | 99.7 |
| 8 | 85.8 | 83.4 | 100 |
| 9 | 28.0 | 37.9 | 79.8 |
| 10 | 23.0 | 41.4 | 65.3 |
| 11 | 18.9 | 55.2 | 61.5 |
| 12 | 1.7 | 37.3 | 32.2 |
| 13 | 8.4 | 48.5 | 46.4 |

It is thus observed that noteworthy efficacy, which may last for two months or more, is obtained.

What is claimed is:

1. A process for the control or elimination of external parasites from cattle and sheep, comprising topically applying, at least monthly, to a localized region on the back of the cattle or sheep, and diffusion therefrom over the animal's body and/or in the sebaceous glands of the animal and thereby obtain said control or elimination, a parasitically effective amount of a direct pour-on skin solution comprising from 0.05 to 25% weight/volume, relative to the total solution, of a compound of formula (I):

wherein:
$R_1$ is CN;
$R_2$ is $S(O)_n R_3$;
$R_3$ is haloalkyl;
$R_4$ represents $NH_2$;
$R_{11}$ represents a halogen atom;
X is C—$R_{12}$;
$R_{12}$ represents a halogen atom;
$R_{13}$ represents a haloalkyl;
n represents an integer equal to 0, 1 or 2
wherein the compound of formula (I) is formulated in a direct pour-on skin solution comprising the compound (I), for application in a volume of 5 to 20 ml per kg of animal, and designed to release the compound (I) onto the skin and the hairs for a contact action against the parasites;
and said solution contains a vehicle or diluent and optionally one or more of: a solvent, and an emollient and/or spreading agent and/or film-forming agent;
wherein the vehicle or diluent is oily;
wherein the organic solvent is selected from the group consisting of acetyltributyl citrate, fatty acid esters, acetone, acetonitrile, benzyl alcohol, butyl diglycol, dimethyl-acetamide, dimethylformamide, dipropylene glycol n-butyl ether, ethanol, isopropanol, methanol, etyhlene glycol monoethyl ether, ethylene glycol monomethyl ether, monomethylacetamide, dipropylene glycol monomethyl ether, liquid polyoxyethylene glycols, propylene glycol, 2-pyrrolidone, N-methylpyrrolidone, diethylene glycol monoethyl ether, ethylene glycol and diethyl phthalate, and combinations thereof; and
wherein the emollient and/or spreading agent and/or film forming agent is selected from the group consisting of:
polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters, lecithin, sodium carboxymethylcellulose, silicone oils, polydiorganosiloxane oils, polydimethylsiloxane oils,
anionic surfactants selected from the group consisting of alkaline stearates, sodium stearate, potassium stearate, ammonium stearate, calcium stearate, triethanolamine stearate, sodium abietate, alkyl sulphates, sodium lauryl sulphate and sodium cetyl sulphate, sodium dodecylbenzenesulphonate, sodium dioctylsulphosuccinate, fatty acids, and fatty acids derived from coconut oil, cationic surfactants selected from the group consisting of water-soluble quaternary ammonium salts of formula $N^+R'R''R'''R''''$, $Y^-$ in which the radicals R are optionally hydroxylated hydrocarbon radicals and $Y-$ is an anion of a strong acid, amine salts of the formula $N^+R'R''R'''$ in which the radicals R are optionally hydrolated hydrocarbon radicals, nonionic surfactans such as sorbitan esters, which are optionally polyoxyethylenated, polyoxyethylenated alkyl ethers, polyoxypropylated fatty alcohols, polyoxyethylenated derivates of castor oil, polyglycerol esters, polyoxyethylenated fatty alcohols, polyoxyethylenated fatty acids, and copolymers of ethylene oxide and propylene oxide, amphoteric surfactants including substituted lauryl compounds of betaine, and combinations thereof.

2. A process for distributing an active agent over the body of cattle or sheep and/or in sebaceous glands of the cattle or sheep, and thereby control external parasites on or eliminate external parasites from the cattle or sheep, comprising topically applying, at least monthly, to a localized region on the back of the cattle or sheep, and diffusion therefrom over the animal's body, a parasitically effective amount of a direct pour-on skin solution comprising the active agent comprising at least one compound corresponding to formula (I):

wherein $R_1$ is CN, $R_2$ is $S(O)_nR_3$, $R_3$ is haloalkyl, $R_4$ is $NH_2$, $R_{11}$, is a halogen atom, X is C—$R_{12}$, $R_{12}$ is a halogen atom, $R_{13}$ is haloalkyl, and n is an integer equal to 0, 1 or 2;

wherein the compound of formula (I) is formulated in a direct pour-on skin solution comprising the compound (I), for application in a volume of 5 to 20 ml per kg of animal, and designed to release the compound (I) onto the skin and the hairs for a contact action against the parasites;

and said solution contains a vehicle or diluent and optionally one or more of: a solvent, and an emollient and/or spreading agent and/or film-forming agent;

wherein the vehicle or diluent is oily;

wherein the organic solvent is selected from the group consisting of acetyltributyl citrate, fatty acid esters, acetone, acetonitrile, benzyl alcohol, butyl diglycol, dimethyl-acetamide, dimethylformamide, dipropylene glycol n-butyl ether, ethanol, isopropanol, methanol, etyhlene glycol monoethyl ether, ethylene glycol monomethyl ether, monomethylacetamide, dipropylene glycol monomethyl ether, liquid polyoxyethylene glycols, propylene glycol, 2-pyrrolidone, N-methylpyrrolidone, diethylene glycol monoethyl ether, ethylene glycol and diethyl phthalate, and combinations thereof; and wherein the emollient and/or spreading agent and/or film forming agent is selected from the group consisting of: polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters, lecithin, sodium carboxymethylcellulose, silicone oils, polydiorganosiloxane oils, polydimethylsiloxane oils, anionic surfactants selected from the group consisting of alkaline stearates, sodium stearate, potassium stearate, ammonium stearate, calcium stearate, triethanolamine stearate, sodium abietate, alkyl sulphates, sodium lauryl sulphate and sodium cetyl sulphate, sodium dodecylbenzenesulphonate, sodium dioctylsulphosuccinate, fatty acids, and fatty acids derived from coconut oil, cationic surfactants selected from the group consisting of water-soluble quaternary ammonium salts of formula $N^+R'R''R'''R''''$, $Y^-$ in which the radicals R are optionally hydroxylated hydrocarbon radicals and $Y-$ is an anion of a strong acid, amine salts of the formula $N^+R'R''R'''$ in which the radicals R are optionally hydrolated hydrocarbon radicals, nonionic surfactans selected from the group consisting of sorbitan esters, which are optionally polyoxyethylenated, polyoxyethylenated alkyl ethers, polyoxypropylated fatty alcohols, polyoxyethylenated derivates of castor oil, polyglycerol esters, polyoxyethylenated fatty alcohols, polyoxyethylenated fatty acids, and copolymers of ethylene oxide and propylene oxide, amphoteric surfactants including substituted lauryl compounds of betaine, and combinations thereof.

3. The process according to claim 1 or 2, wherein the external parasite is a tick.

4. The process according to claim 1 or 2, wherein the external parasite is *Boophilus microplus* in cattle, and lice and blowfly in sheep.

5. The process according to claim 1 or 2, wherein the solution is applied in a volume of 5 to 20 ml per 100 kg of animal.

6. The process according to claim 1 or 2, wherein the solution is applied in a volume of about 10 ml per 100 kg of animal.

7. The process according to claim 1 or 2, wherein the solution is applied with a total volume of from 10 to 150 ml per animal.

8. The process according to claim 1 or 2, wherein $R_{13}$ is $CF_3$.

9. The process according to claim 1 or 2, wherein n=1 and $R_3$ is $CF_3$.

10. The process according to claim 1 or 2, wherein n=0 and $R_3$ is $CF_3$.

11. The process according to claim 1 or 2, wherein the compound of formula (I) is present in an amount of from 0.05 to 10% weight/volume.

12. The process according to claim 1 or 2, wherein the compound of formula (I) is present in an amount of from 0.1 to 2%.

13. The process according to claim 1 or 2, wherein the compound of formula (I) is present in an amount of from 0.25 to 1.5%.

14. The process according to claim 1 or 2, wherein the compound of formula (I) is present in an amount of about 1%.

15. The process according to claim 1 or 2, wherein one applies the solution in an amount of from 0.1 to 2 mg/kg.

16. The process according to claim 1 or 2, wherein one applies the solution in an amount of from 0.25 to 1.5 mg/kg.

17. The process according to claim 1 or 2, wherein one applies the solution in an amount of about 0.1 mg/kg.

18. The process according to claim 1 or 2, wherein one applies the solution to the animals in pasture or before they arrive in pasture.

19. The process according to claim 1 or 2, wherein one applies the solution to the animals before they arrive in the Feed Lot, this application being the final one before the animal is slaughtered.

20. The process according to claim 1 or 2, wherein the solution provides total elimination of *Boophilus microplus* in less than 2 days.

21. The process of claim 1or 2, wherein the applying ceases from between 1 to 3 months prior to slaughter.

22. The process of claim 1 or 2, wherein the applying ceases from between 1.5 and 2.5 months prior to slaughter.

23. The process of claims 22, wherein the applying ceases at about 2 months prior to slaughter.

24. The process of claim 22, wherein the solution is an oily solution.

25. The process of claim 1 or 2, wherein the solution comprises a solvent for at least one compound, and a diluent, and optionally an emollient.

26. The process of claim 25, wherein the emollient is present in a proportion of from 0.1 to 10% by volume.

27. The process of claim 25, wherein the emollient is present in an amount of from 0.25 to 5% by volume.

28. The process of claim 25, wherein the solvent is selected from the group consisting of acetyl tributyl citrate, fatty acid esters, diisobutyl adipate, acetone, acetonitrile, benzyl alcohol, butyl diglycol, dimethylacetamide, dimethylformamide, diporpylene glycol n-butyl ether, ethanol, isopropanol, methanol, ethylene glycol monoethyl ether, ethylene glycol monomethyl ether, monomethylacetamide, diporpylene glycol monomethyl ether, liquid polyoxyethylene glycols, proplyene glycol, 2-pyrrolidone, N-methylpyrrolidone, diethylene glycol monoethyl ether, ethylene glycol and diethyl phthalate, or a mixture of at least two of those solvents.

29. The process according to claim 25, wherein the diluent is selected from the group consisting of plant oils, mineral oils, aliphatic or cyclic hydrocarbons.

30. The process according to claim 25, wherein the emollient is selected from the group consisting of polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, anionic surfactants sodium, potassium or ammonium stearates; calcium stearate, triethanolamine stearate; sodium abietate; alkyl sulphates, in particular sodium lauryl sulphate and sodium cetyl sulphate; sodium dodecylbenzenesulphonate, sodium dioctylsulphosuccinate; and fatty acids, cationic surfactants, amine salts of formula N⁺R'R"R'" in which the radicals R are optionally hydroxylated hydrocarbon radicals; octadecylamine hydrochloride is among the cationic surfactants which can be used, nonionic surfactants, amphoteric surfactants; and a mixture of at least two of these agents.

31. A process for the control or elimination of external parasites from cattle and sheep, comprising topically applying, to a localized region on the back of the cattle or sheep, and diffusion therefrom over the animal's body and/or in the sebaceous glands of the animal and thereby obtain said control or elimination, a parasitically effective amount of a direct pour-on skin solution comprising from 0.05 to 25% weight/volume, relative to the total solution, of a compound of formula (I):

wherein:
   $R_1$ is CN;
   $R_2$ is $S(O)_n R_3$;
   $R_3$ is haloalkyl;
   $R_4$ represents $NH_2$;
   $R_{11}$ represents a halogen atom;
   X is C—$R_{12}$;
   $R_{12}$ represents a halogen atom;
   $R_{13}$ represents a haloalkyl;
   n represents an integer equal to 0, 1 or 2;
   wherein the compound of formula (I) is formulated in a direct pour-on skin solution comprising the compound (I), for application in a volume of 5 to 20 ml per kg of animal, and designed to release the compound (I) onto the skin and the hairs for a contact action against the parasites;
   and said solution contains a vehicle or diluent and optionally one or more of: a solvent, and an emollient and/or spreading agent and/or film-forming agent;
   wherein the vehicle or diluent is oily;
   wherein the organic solvent is selected from the group consisting of acetyltributyl citrate, fatty acid esters, acetone, acetonitrile, benzyl alcohol, butyl diglycol, dimethyl-acetamide, dimethylformamide, dipropylene glycol n-butyl ether, ethanol, isopropanol, methanol, etyhlene glycol monoethyl ether, ethylene glycol monomethyl ether, monomethylacetamide, dipropylene glycol monomethyl ether, liquid polyoxyethylene glycols, propylene glycol, 2-pyrrolidone, N-methylpyrrolidone, diethylene glycol monoethyl ether, ethylene glycol and diethyl phthalate, and combinations thereof; and
   wherein the emollient and/or spreading agent and/or film forming agent is selected from the group consisting of:
      polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters, lecithin, sodium carboxymethylcellulose, silicone oils, polydiorganosiloxane oils, polydimethylsiloxane oils,
      anionic surfactants selected from the group consisting of alkaline stearates, sodium stearate, potassium stearate, ammonium stearate, calcium stearate, triethanolamine stearate, sodium abietate, alkyl sulphates, sodium lauryl sulphate and sodium cetyl sulphate, sodium dodecylbenzenesulphonate, sodium dioctylsulphosuccinate, fatty acids, and fatty acids derived from coconut oil, cationic surfactants selected from the group consisting of water-soluble quaternary ammonium salts of formula $N^+R'R''R'''R''''$, $Y^-$ in which the radicals R are optionally hydroxylated hydrocarbon radicals and $Y-$ is an anion of a strong acid, amine salts of the formula $N^+R'R''R'''$ in which the radicals R are optionally hydrolated hydrocarbon radicals, nonionic surfactans such as sorbitan esters, which are optionally polyoxyethylenated, polyoxyethylenated alkyl ethers, polyoxypropylated fatty alcohols, polyoxyethylenated derivates of castor oil, polyglycerol esters, polyoxyethylenated fatty alcohols, polyoxyethylenated fatty acids, and copolymers of ethylene oxide and propylene oxide, amphoteric surfactants including substituted lauryl compounds of betaine, and combinations thereof;

wherein one applies the solution every two months.

32. A process for the control or elimination of external parasites from cattle and sheep, comprising topically applying, to a localized region on the back of the cattle or sheep, and diffusion therefrom over the animal's body and/or in the sebaceous glands of the animal and thereby obtain said control or elimination, a parasitically effective amount of a direct pour-on skin solution comprising from 0.05 to 25% weight/volume, relative to the total solution, of a compound of formula (I):

wherein:
$R_1$ is CN;
$R_2$ is $S(O)_n R_3$;
$R_3$ is haloalkyl;
$R_4$ represents $NH_2$;
$R_1$ represents a halogen atom;
X is $C-R_{12}$,
$R_{12}$ represents a halogen atom;
$R_{13}$ represents a haloalkyl;
n represents an integer equal to 0, 1 or 2;
wherein the compound of formula (I) is formulated in a direct pour-on skin solution comprising the compound (I), for application in a volume of 5 to 20 ml per kg of animal, and designed to release the compound (I) onto the skin and the hairs for a contact action against the parasites;

and said solution contains a vehicle or diluent and optionally one or more of: a solvent, and an emollient and/or spreading agent and/or film-forming agent;

wherein the vehicle or diluent is oily;

wherein the organic solvent is selected from the group consisting of: acetyltributyl citrate, fatty acid esters, acetone, acetonitrile, benzyl alcohol, butyl diglycol, dimethyl-acetamide, dimethylformamide, dipropylene glycol n-butyl ether, ethanol, isopropanol, methanol, etyhlene glycol monoethyl ether, ethylene glycol monomethyl ether, monomethylacetamide, dipropylene glycol monomethyl ether, liquid polyoxyethylene glycols, propylene glycol, 2-pyrrolidone, N-methylpyrrolidone, diethylene glycol monoethyl ether, ethylene glycol and diethyl phthalate, and combinations thereof; and wherein the emollient and/or spreading agent and/or film forming agent is selected from the group consisting of:
polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters, lecithin, sodium carboxymethylcellulose, silicone oils, polydiorganosiloxane oils, polydimethylsiloxane oils, anionic surfactants selected from the group consisting of alkaline stearates, sodium stearate, potassium stearate, ammonium stearate, calcium stearate, triethanolamine stearate, sodium abietate, alkyl sulphates, sodium lauryl sulphate and sodium cetyl sulphate, sodium dodecylbenzenesulphonate, sodium dioctylsulphosuccinate, fatty acids, and fatty acids derived from coconut oil, cationic surfactants selected from the group consisting of water-soluble quaternary ammonium salts of formula $N^+R'R''R'''R''''$, $Y^-$ in which the radicals R are optionally hydroxylated hydrocarbon radicals and $Y-$ is an anion of a strong acid, amine salts of the formula $N^+R'R''R'''$ in which the radicals R are optionally hydrolated hydrocarbon radicals, nonionic surfactans selected from the group consisting of sorbitan esters, which are optionally polyoxyethylenated, polyoxyethylenated alkyl, ethers, polyoxypropylated fatty alcohols, polyoxyethylenated derivates of castor oil, polyglycerol esters, polyoxyethylenated fatty alcohols, polyoxyethylenated fatty acids, and copolymers of ethylene oxide and propylene oxide, amphoteric surfactants including substituted lauryl compounds of betaine, and combinations thereof, wherein when applied topically locally onto the animal's skin, the solution is designed to ensure protection for at least two months, in particular against *Boophilus microplus.*

* * * * *

UNITED STATES PATENT AND TRADEMARK OFFICE
CERTIFICATE OF CORRECTION

PATENT NO. : 6,413,542 B1
DATED : July 2, 2002
INVENTOR(S) : Jean-Pierre Etchegaray et al.

It is certified that error appears in the above-identified patent and that said Letters Patent is hereby corrected as shown below:

Column 18,
Line 11, change "etyhlene" to -- ethylene --.

Signed and Sealed this

Third day of September, 2002

Attest:

JAMES E. ROGAN
Attesting Officer
Director of the United States Patent and Trademark Office